(12) United States Patent
Wagner (10) Patent No.: US 6,256,097 B1
(45) Date of Patent: Jul. 3, 2001

(54) ELLIPSOMETER AND ELLIPSOMETRY METHOD

(75) Inventor: Jeff A. Wagner, Long Valley, NJ (US)

(73) Assignee: Rudolph Technologies, Inc., Flanders, NJ (US)

( * ) Notice: Subject to any disclaimer, the term of this patent is extended or adjusted under 35 U.S.C. 154(b) by 0 days.

(21) Appl. No.: 09/478,795

(22) Filed: Jan. 7, 2000

Related U.S. Application Data
(60) Provisional application No. 60/115,354, filed on Jan. 8, 1999.

(51) Int. Cl.$^7$ ..................................................... G01J 4/00
(52) U.S. Cl. ............................................. 356/369; 250/226
(58) Field of Search ..................................... 356/364, 365, 356/366, 367, 368, 369, 345, 351; 250/225, 226, 559–560, 559.27, 559.23

(56) References Cited

U.S. PATENT DOCUMENTS

| | | | |
|---|---|---|---|
| 5,018,861 | * | 5/1991 | Remo ..................................... 356/353 |
| 5,166,752 | * | 11/1992 | Spanier et al. ......................... 356/369 |
| 5,519,493 | * | 5/1996 | Reiley ................................... 356/367 |
| 5,610,392 | * | 3/1997 | Nayagama et al. .................... 250/226 |
| 5,933,236 | * | 8/1999 | Sommargren .......................... 356/354 |

\* cited by examiner

Primary Examiner—Frank G. Font
Assistant Examiner—Sang H. Nguyen
(74) Attorney, Agent, or Firm—Antonelli, Terry, Stout & Kraus, LLP

(57) ABSTRACT

An improved ellipsometry method and a self-correcting simultaneous multiple angle/multiple wavelength return path ellipsometer are disclosed which allow for simultaneous measurement at multiple angles of incidence in a manner which permits separation of instrument error from the measured properties. In the method polarized light from a single beam of light is simultaneously directed to interact with an optical system under study at different angles of incidence and the change of polarization state is measured for at least one and preferably each of a plurality of the angles of incidence. Non-sample optical system ellipsometric effects of the ellipsometer are measured and the measured changes in polarization state are corrected to eliminate errors introduced thereby. The disclosed embodiment is self-correcting by way of a convex reflector which can be inserted into and removed from the optical path of the beam of polarized light between a focusing optic and the sample optical system under study. The convex reflector when inserted into the optical path causes the light rays of the beam of polarized light in each of the plurality of angles of incidence to retrace its path through the focusing optic for detection by a detector array without undergoing reflection and re-reflection as during a sample measurement configuration of the ellipsometer where the convex reflector is removed from the optical path.

41 Claims, 8 Drawing Sheets

ELLIPSOMETER AND ELLIPSOMETRY METHOD

RELATED APPLICATION

This application claims priority of the prior, copending provisional application Serial No. 60/115,354, filed Jan. 8, 1999.

FIELD OF THE INVENTION

The present invention relates to an ellipsometer and an ellipsometry method for ellipsometric measurements using a focused measurement beam at single or multiple nominal angles of incidence and/or multiple wavelengths, for measuring the change in polarization state of light upon interaction with a sample for determining characteristics of the sample.

BACKGROUND AND SUMMARY OF THE INVENTION

Ellipsometry is an optical technique for the characterization and observation of events at an interface or film between two media and is based on exploiting the polarization transformation that occurs as a beam of polarized light is reflected from or transmitted through the interface or film. Ellipsometry has been particularly attractive because of its essential non-perturbing character (when the wavelength and intensity of the light beam are properly chosen) hence its suitability for in-situ measurements, and its remarkable sensitivity to minute interfacial effects, such as the formation of a sparsely distributed sub-monolayer of atoms or molecules.

One way in which the light wave can interact with an optical system under study is by being reflected by a surface of the optical system. This reflection causes the state of polarization to be changed abruptly. Such change can be explained using the Fresnel reflection coefficients for the two linear polarizations parallel (p) and perpendicular (s) to the plane of incidence. Reflection ellipsometry has been recognized as an important tool for the study of surfaces and thin films. Among the many useful applications of ellipsometry are:

(1) the measure of optical properties of materials and their frequency dependence (wavelength dispersion), the materials may be in liquid or solid phase, may be optically isotropic or anisotropic, and can be either in bulk or thin-film form;

(2) monitoring of phenomena on surfaces that involve either the growth of thin films starting from a submono-layer (e.g., by oxidation, deposition, absorption or diffusion of impurities), or the removal of such films (e.g., by desorption, sputtering or diffusion); and (3) measurement of physical factors that affect the optical properties such as electric and magnetic fields, stress or temperature. When the polarization state change depends on the angle of interaction of the light beam and the sample under study, as for example with reflection from a sample, the incident light should be as collimated as possible so only a single angle of incidence is measured at one time.

It is advantageous to measure as many angles of incidence on a particular sample as possible. However, in the past this was not done frequently because it is so cumbersome to get the data by making separate successive measurements at each angle through the use of a scanning technique or with multiple ellipsometers. This problem in the art has been overcome by the Assignee's simultaneous multiple angle/multiple wavelength ellipsometer and method as disclosed in its U.S. Pat. No. 5,166,752. The ellipsometry method and the ellipsometer disclosed therein permit the simultaneous illumination of a sample at a whole range of angles of incidence from a single beam of light and permit the rapid, easy collection of a large multiplicity of data for different angles or ranges of angles within the whole range of angles without requiring scanning or the use of multiple ellipsometers. However, a drawback of this known ellipsometry method and ellipsometer is that they do not provide a means for separation of instrument error from the measured properties. This instrument error can be significant, especially where the ellipsometer is vacuum compatible. The disclosure of Assignee's U.S. Pat. No. 5,166,752 is incorporated herein by reference.

Return path or folded-path ellipsometers are, per se, known. O'Bryan, for example, devised a folded-path ellipsometer for making measurements with collimated light interacted with an optical system at a single angle of incidence, see FIG. 3.21 on page 253, and the related discussion, in *Ellipsometry and Polarized Light* by R. A. Azzam and N. M. Bashara, published by North-Holland Physics Publishing, 1987 edition. However, this known return path ellipsometer does not allow for simultaneous measurements at multiple angles of incidence and/or multiple wavelengths.

There is a need for an improved ellipsometry method and ellipsometer which overcome the aforementioned disadvantages and limitations of the prior art. An object of the present invention is to provide an improved ellipsometry method and ellipsometer which solve these problems and, at the same time, which offer more accurate measurements, more measurement capability and simplicity as compared with the prior art.

These and other objects of the invention are attained by the ellipsometry method of the invention which comprises operating an ellipsometer to direct polarized light so that it interacts with a sample optical system under study, and measuring the change in polarization state of light interacted with the sample optical system, the polarized light from a single beam of light being simultaneously directed to interact with the sample optical system at different angles of incidence. The change of polarization state is measured for at least one, and preferably each of a plurality of the angles of incidence. The method further includes measuring non-sample optical system ellipsometric effects of the ellipsometer and using the results thereof to correct the measured changes in polarization state to eliminate error that is introduced by the non-sample optical system ellipsometric effects.

In the disclosed embodiment, the step of measuring non-sample optical system ellipsometric effects of the ellipsometer includes operating the ellipsometer in an error correction mode during which the sample optical system under study is effectively removed from the optical path of the ellipsometer. As a result of the nature of the ellipsometry method and ellipsometer of the invention, the ellipsometric measurements made in the error correction mode and those made with the sample optical system under study, e.g. the sample, in the optical path of the ellipsometer differ only in that the measurement performed during sample measurement includes interactions with the measured sample. All aspects of the measurement which are related to imperfections in the apparatus, e.g. the non-sample optical system ellipsometric effects, are common to both measurements and are therefore subject to elimination by appropriate mathematical technique as discussed herein.

The ellipsometry method of the invention preferably involves operating a return-path ellipsometer with a polarizer arm and an analyzer arm superimposed on or sharing components with the polarizer arm and wherein the step of directing the polarized light to interact with the sample optical system at a plurality of angles of incidence includes reflecting the light from a surface of the sample optical system and re-reflecting the reflected light from the surface of the sample optical system so that it retraces its path in the arm of the ellipsometer. In this way, the light interacts twice with the surface of the sample.

The step of measuring non-sample optical system ellipsometric effects of the ellipsometer preferably includes inserting a reflector in the optical path of the beam of polarized light directed toward the sample optical system at different angles of incidence to cause the light rays at each of the plurality of angles of incidence in the beam to retrace its path in the arm of the ellipsometer without undergoing reflection and re-reflection from the surface of the optical system as in the sample measurement step. The reflector is removed from the optical path of the beam of polarized light directed toward the optical system to permit the measuring of the change in polarization state of the light interacted with the sample optical system. In one example of the invention, a thin film under study is supported on a stage of the ellipsometer in a manner to permit adjustment of the position of the film with respect to the focusing optic of the ellipsometer. This enables the relative position of the film and focusing optic to be adjusted so that preferably the focused beam of polarized light is reflected and re-reflected from the same spot on the surface of the film.

Further, in the disclosed embodiment of the method, the polarization state of the light beam is modulated during each of the measuring steps. A portion of the light which is re-reflected to the focusing optic reaches a detector array of the ellipsometer where the intensity of a multiplicity of constituent rays, each corresponding to a different angle of incidence on the sample, is measured as a function of time. This information is sufficient to determine the ellipsometric properties of the sample at each of the angles of incidence in accordance with standard practice.

The improved ellipsometer of the invention comprises means for directing polarized light so that it interacts with a sample optical system under study, and means for measuring the change in polarization state of the light interacted with the sample optical system under study, wherein the means for directing polarized light includes means for simultaneously directing polarized light from a single beam of light onto the optical system under study at different angles of incidence and wherein the means for measuring measures the change in polarization state of light interacted with the sample optical system under study for at least one, and preferably for each of a plurality, of the different angles of incidence. Further, the ellipsometer includes means for measuring non-sample optical system ellipsometric effects of the ellipsometer to allow correction of the measured changes in polarization state of the light interacted with the optical system to eliminate error introduced therein by the non-sample optical system ellipsometric effects. The means for measuring non-sample optical system ellipsometric effects includes means for operating the ellipsometer in an error correction mode as mentioned above.

More particularly, in the disclosed embodiment, the ellipsometer is a return-path ellipsometer having a polarizer arm and an analyzer arm superimposed on the polarizer arm and wherein the means for measuring the change in polarization state of light interacted with the sample optical system under study for each of the plurality of angles of incidence reflects the light from a surface of the optical system and re-reflects the reflected light from the surface of the sample optical system so that it retraces its path in the arm of the ellipsometer for detection by the detector array. In the disclosed embodiment, the means for measuring non-sample optical system ellipsometric effects includes a reflector which can be automatically inserted in a position in the optical path of the beam of polarized light directed toward the sample optical system at different angles of incidence to cause the light rays at each of the plurality of angles of incidence in the beam to retrace its path in the arm of the ellipsometer without undergoing the reflection and re-reflection from the surface of the sample optical system.

The reflector in the disclosed embodiment is a convex mirror having a center of negative curvature thereof coincident with a focal point of a focusing optic of the ellipsometer focusing the single beam of light at a single point on the sample optical system with constituent light rays forming the plurality angles of incidence with the sample optical system. A mechanism is also provided for moving the reflector into and out of the position in the optical path. The position is proximate the optical system under study in the disclosed example. These and other objects, advantages and features of the present invention will become more apparent from the following detailed description of several embodiments of the invention taken with the accompanying drawings.

The method and ellipsometer of the invention are not limited to multi-angle ellipsometry but have applicability to return path ellipsometry and return path ellipsometers for allowing correcting for non-sample optical system ellipsometric effects such as that induced by a vacuum-window where the ellipsometer is vacuum compatible.

DETAILED DESCRIPTION OF DISCLOSED EMBODIMENTS

Referring now to the drawings, an ellipsometer 20, illustrated in FIGS. 1–5 of the drawings is a self-correcting simultaneous multiple angle return-path ellipsometer. The ellipsometer 20 comprises a monochromatic or polychromatic collimated light source 1, beam shaping optics including but not limited to a spatial filtering beam expander 2, and a fixed polarizer 3, which provide a beam of polarized light. A polarization modulation section 4 of the ellipsometer includes a means for modulating the polarization state of the light beam, for example a rotating or oscillating retarder, a rotating or oscillating polarizer, or a photoelastic modulator. A focusing optic 5, consisting of one or more elements of either transmissive or reflective type, forms a focus at the surface of the sample 7 to be measured. The sample is held on a stage or chuck 16 of the ellipsometer. The angles of incidence in the focused beam vary over a range of angles of at least one or two degrees, and preferably as in the illustrated preferred embodiment, the range of angles of incidence is 30 degrees as discussed in U.S. Pat. No. 5,166,752. The focused beam is entirely oblique to the surface of the sample 7. The light is focused by the focusing optic 5 to a single small spot or point on the surface of sample 7. The diameter of the spot is preferably less than or equal to 10 microns.

Figure 1:
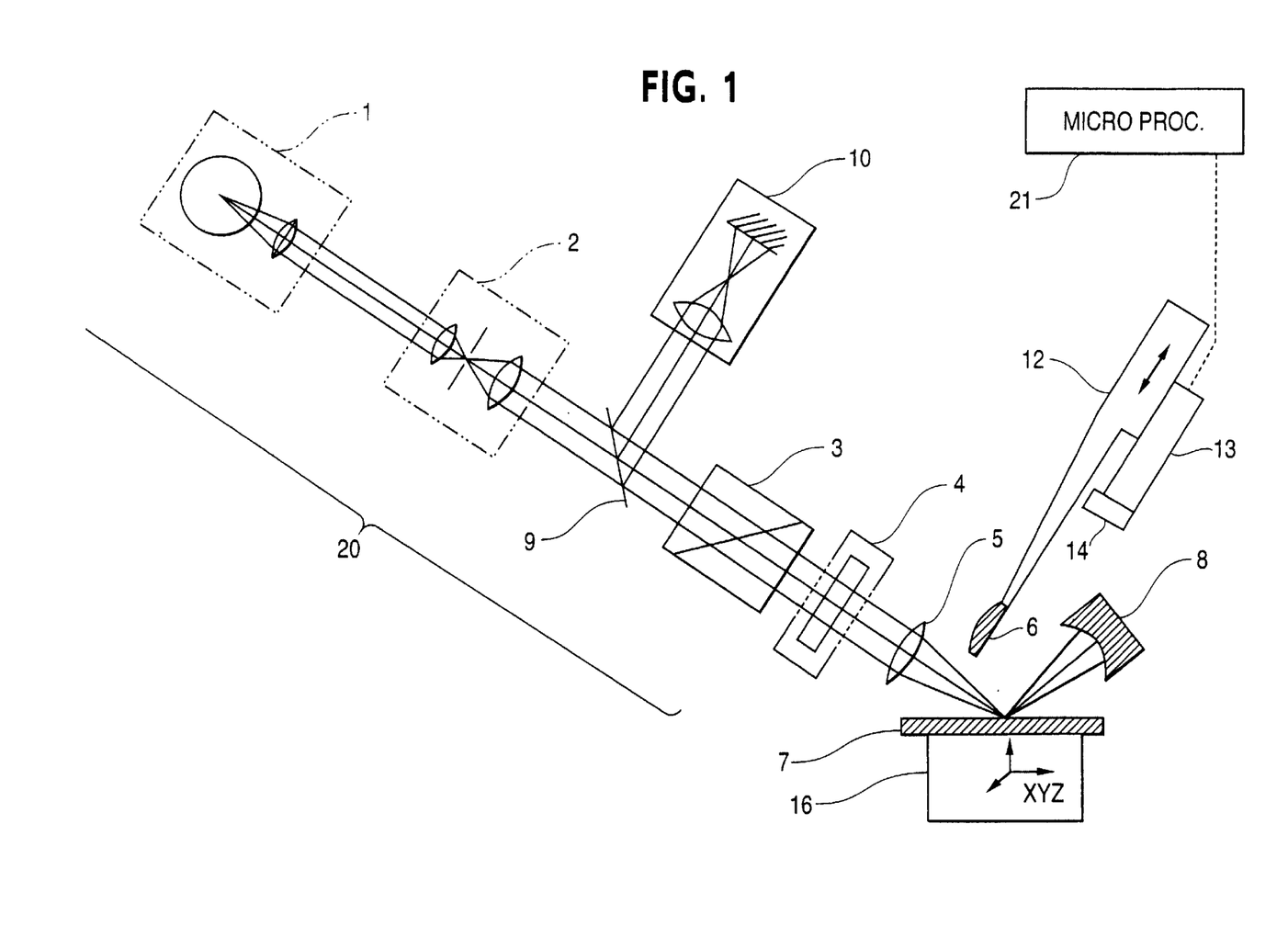
FIG. 1 a schematic illustration of a self-correcting multiple angle return-path ellipsometer according to a preferred embodiment of the invention, the ellipsometer being shown in a sample measurement configuration thereof.
Figure 2:
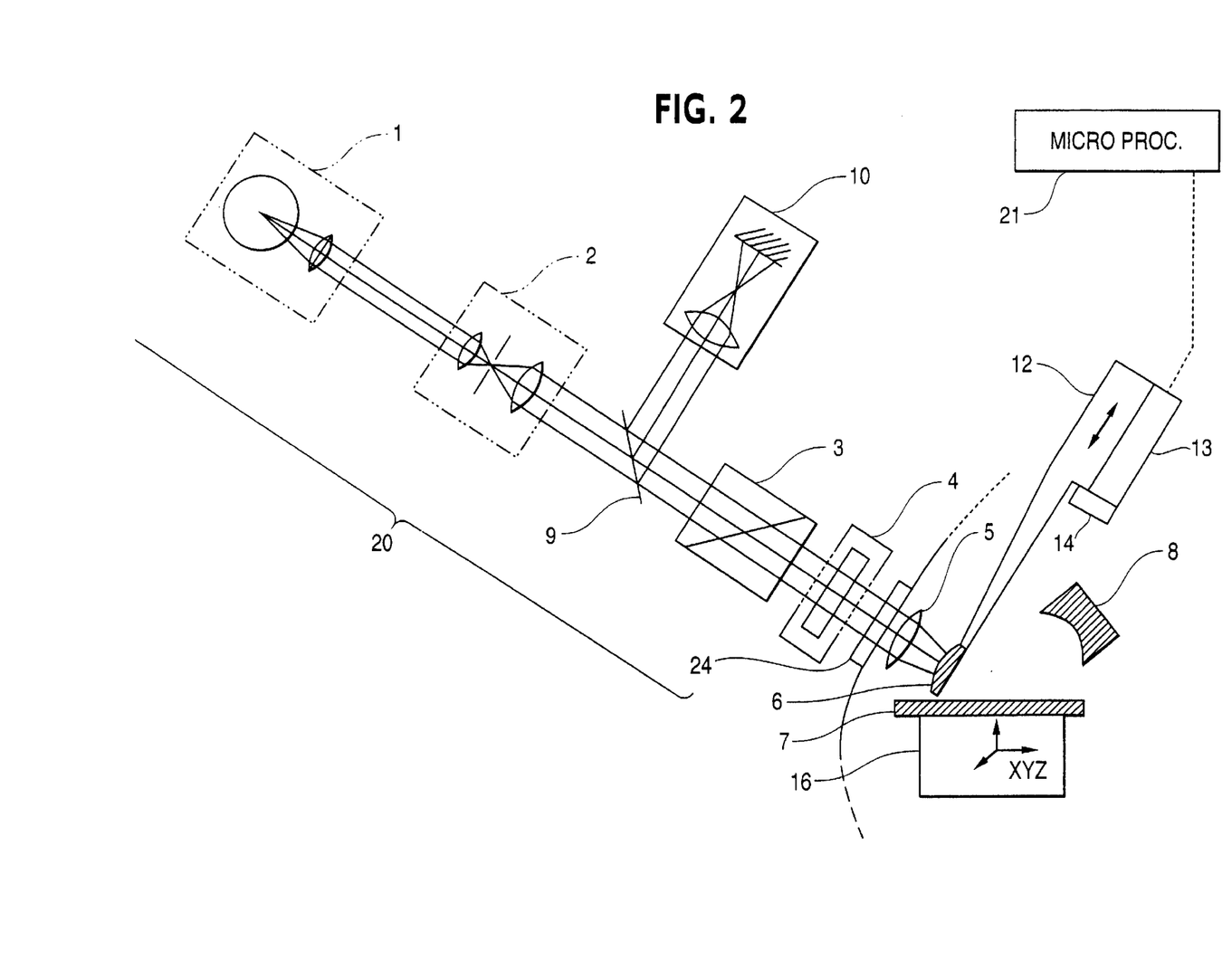
FIG. 2 is a schematic illustration of the ellipsometer of FIG. 1 wherein the ellipsometer is depicted in an instrument error correction configuration.
Figure 4:
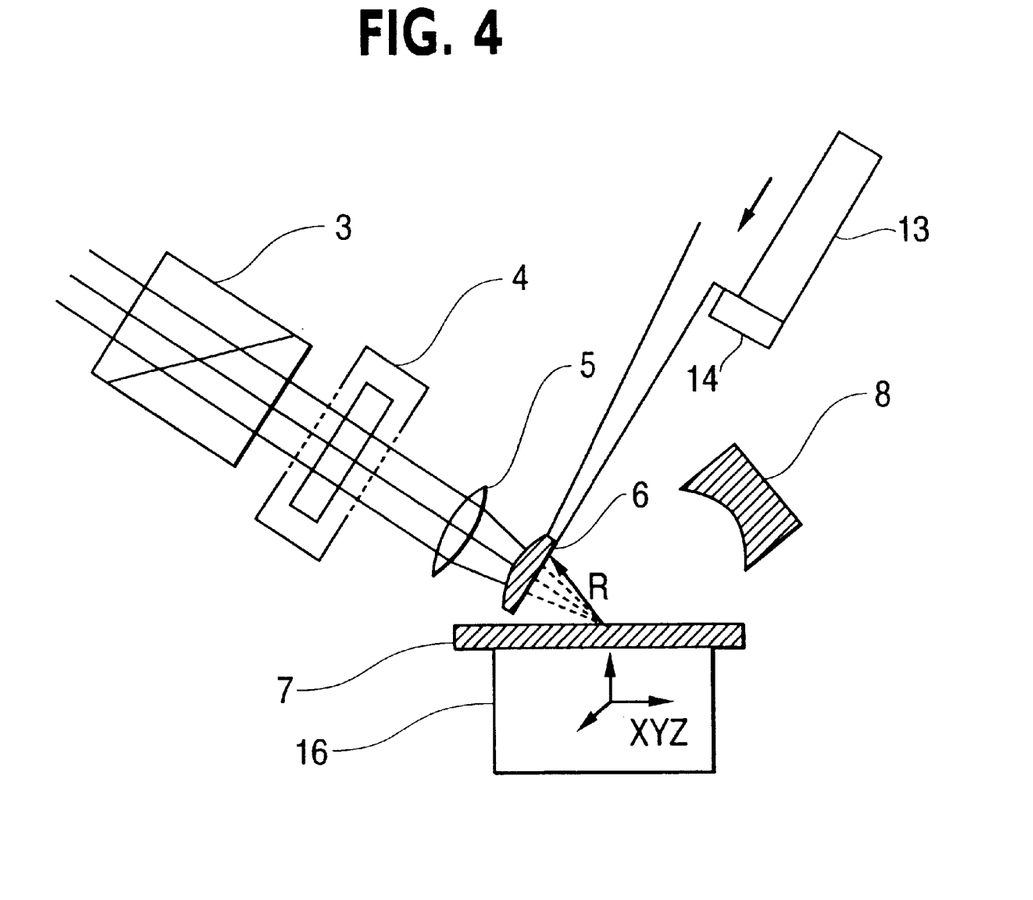
FIG. 4 is an enlarged schematic drawing of a portion of the disclosed ellipsometer showing the convex reflector positioned in the optical path of the focused, polarized light beam and the relationship of its center of negative curvature with a focal point of the focusing optic in the ellipsometer.
Figure 5:
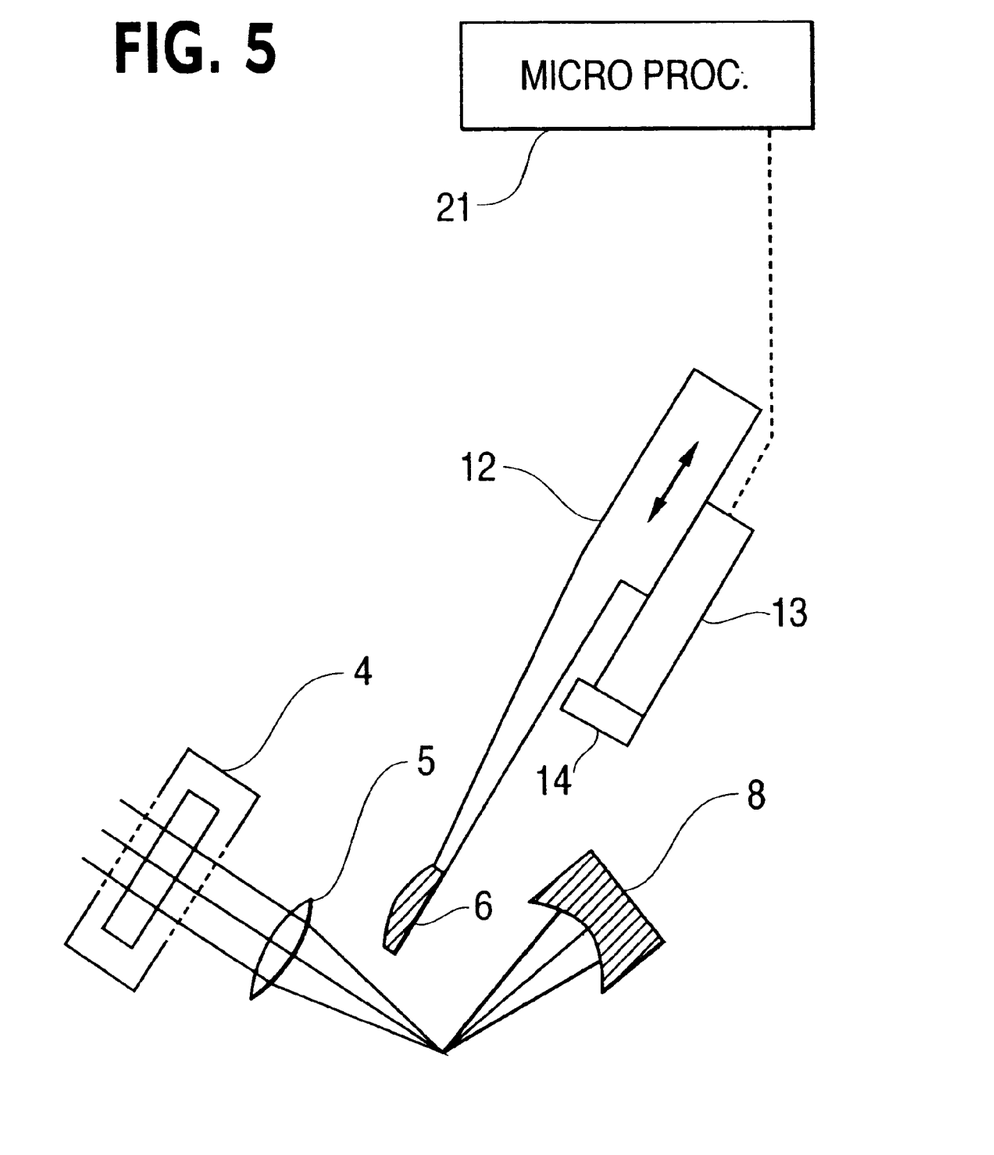
FIG. 5 is a schematic drawing of the mechanism for inserting and removing the convex reflector of the ellipsometer from the optical path of the focused, polarized beam of light, the mechanism including a bearing and a hard stop for precisely positioning the convex reflector in a predetermined position in the optical path during ellipsometry measurements in the instrument error correction configuration thereof.

A convex reflector in the form of a convex mirror 6 is inserted into and removed from the optical path by means of an automated mechanism 12 controlled by a suitably programmed microprocessor 21. The mechanism 12 includes a bearing 13 and a hard stop 14 for precisely positioning the convex reflector in the predetermined position in the optical path during operation of the ellipsometer in an instrument error correction configuration as depicted in FIGS. 2, 4 and 5. The stage or chuck 16 holding the sample 7 is preferably adjustable in the x, y and z directions as shown in FIG.1. A fixed concave reflector in the form of a concave mirror 8 is also provided in the ellipsometer along with a beam splitting optic 9 and a square or linear array detector 10 with associated imaging optics.

The ellipsometer of the disclosed embodiment of the invention is operated in two configurations. First, a sample measurement configuration (FIG. 1) during which the convex mirror 6 is removed from the optical path and second, and an instrument error correction configuration (FIG. 2), during which the convex mirror is inserted in the optical path effectively removing the measured sample 7 and concave mirror 8 from the optical system.

Figure 3:
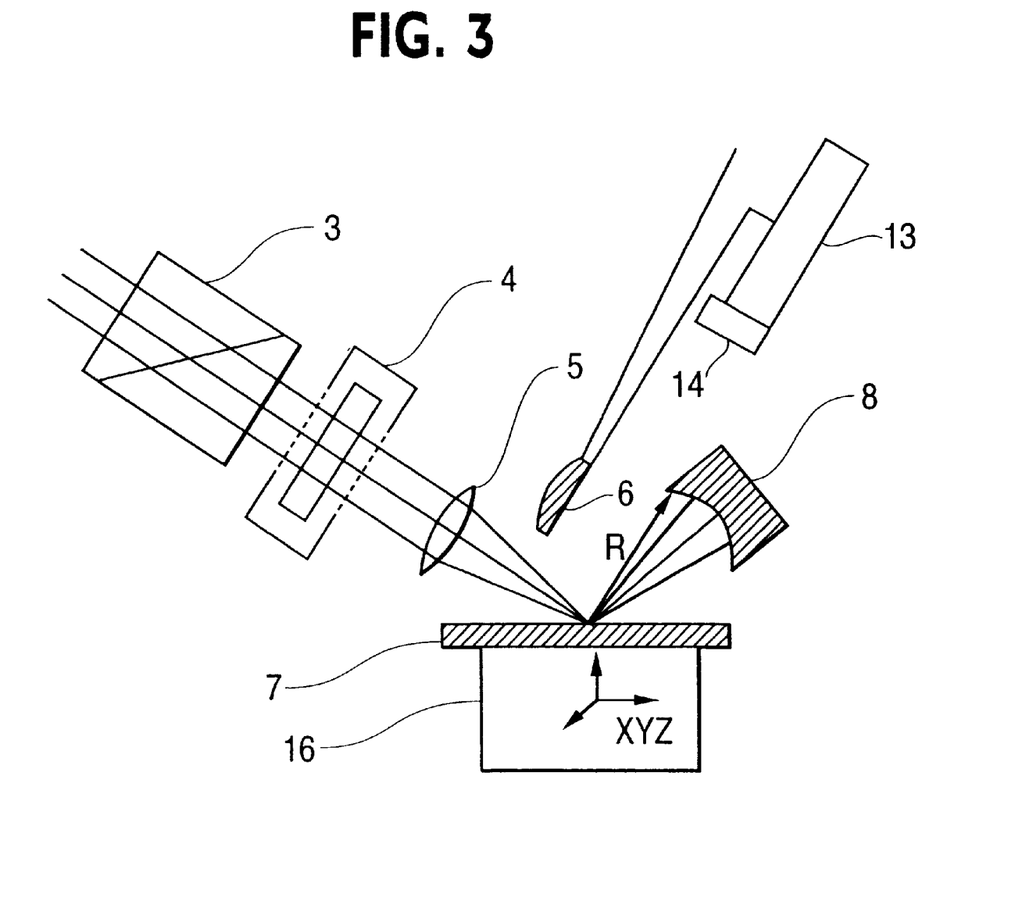
FIG. 3 is an enlarged schematic drawing of the portion of the ellipsometer of FIGS. 1 and 2 showing the concave reflector and the location of its center of curvature.

During operation in the sample measurement configuration (FIG. 1), light from the light source 1 passes through the beam shaping optics 2 and is linearly polarized by the fixed polarizer 3. The polarization state of the light is modulated by the polarization modulation section 4. The light is then focused by the focusing optic 5 so as to arrive at a single point on the measured sample with the constituent light rays forming a multiplicity of incidence angles. The light is then reflected at a multiplicity of angles. The light then strikes the fixed concave mirror 8. This mirror is positioned such that its center of curvature is coincident with the illuminated point on the measured sample as illustrated in FIG. 3. This positioning allows each of the constituent rays reflected from the concave mirror to retrace its path through the above-described optical system in reverse order, e.g., it again passes through the optical system. Accordingly, light reflected from the concave mirror 8 returns to the sample 7 arriving at a multiplicity of incidence angles. The light re-flects from the measured sample and is collected by the focusing optic 5 where it is returned to a collimated state. Preferably the focused beam of polarized light is reflected and re-reflected from the same spot on the surface of the sample 7. The light is then further modulated by the polarization modulation section 4 and then passes through the fixed polarizer 3. A portion of the light is then redirected by the beam splitting optic 9 to the array detector 10 where the intensity of a multiplicity of constituent rays, each corresponding to a different angle of incidence on the sample, are measured as a function of time. This information is sufficient to determine the ellipsometric properties of the sample at each of the angles of incidence in accordance with standard practice.

During operation of the ellipsometer 20 in the error instrument correction configuration (FIG. 2), the light proceeds in the apparatus in a manner identical to that described in the sample measurement configuration up to and including the first reference to the focusing optic 5. After passing through the focusing optic 5 the light is reflected from the convex mirror 6. This mirror is positioned such that the center of its negative curvature is coincident with the focal point of the focusing optic 5, see FIG. 4. This positioning allows each of the multiplicity of reflected constituent light rays to retrace its path through the optics of the ellipsometer for detection by the array detector 10 as described in the sample configuration commencing from and including the second reference to the focusing optic 5.

According to the method of the invention, the ellipsometer enables contrasting measurements to be made at each of the two configurations described above. In the sample measurement configuration, after passing through focusing optic 5 the light interacts with the sample 7, the concave mirror 8 and again with the measured sample 7. Alternately, in the instrument error correction configuration, after passing through the focusing optic 5, the light interacts with the convex mirror 6. In both configurations, the interaction of the light with the mirror, either concave or convex, is such that each of the multiplicity of constituent rays strikes the mirror perpendicular to the local surface. Such reflections where the light rays are perpendicular to the reflecting surface, ideally cause only a trivial phase reversal and do not impart ellipsometric light information to the light in a manner related to the detailed nature of the reflecting surface. Therefore, ellipsometric measurements made in each of the two configurations described above differ only in that the measurement performed in the sample measurement configuration includes the two interactions with the measured sample. All aspects of measurement which are related to imperfections in the ellipsometer are common to measurements made in each of the configurations are therefore subject to elimination by the appropriate mathematical technique.

In the field of ellipsometry changes in polarization state are traditionally expressed in terms of two quantities: the relative phase of the s and p components is called delta. The arctangent of the relative amplitude of the s and p components is called psi. Delta errors accumulate in an additive manner. The sample measurement configuration described above measures a total delta equal to twice the delta of the sample plus the delta of the instrument. The error correction configuration measures the delta of the instrument only. Therefore, the error in delta is removed by subtraction of the error correction mode measurements from the sample measurement. Psi errors accumulate by the product of the tangents. The sample measurement configuration measures the square of the tangent of the sample psi multiplied by the tangent of the psi due to instrument error. The error correction configuration measures the tangent of psi due to instrument error alone. Therefore, the error in psi is removed by dividing the tangent of the total psi measured in the sample measurement configuration by the tangent of the psi measured in the instrument correction configuration.

Figure 6:
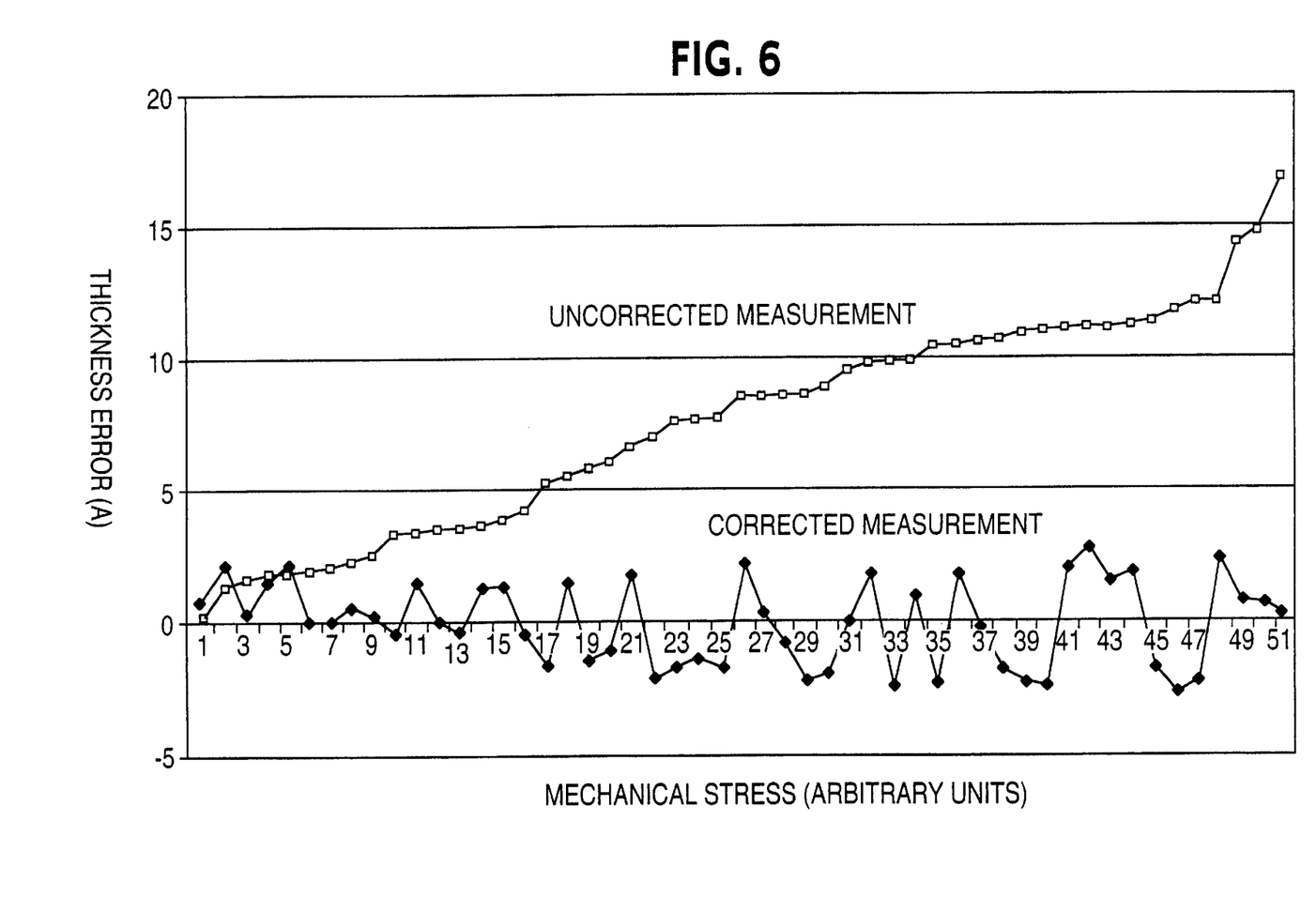
FIG. 6 is a graph of ellipsometric measurements made with the ellipsometer according to the method of the invention including ellipsometric measurements made in the sample measurement configuration and the resultant corrected ellipsometric measurements wherein the sample measurements have been corrected to eliminate the instrument errors therefrom.

More specifically, by way of example, the ellipsometer 20 can be used to make ellipsometric measurements where the sample optical system is a thin film of silicon, 7 in FIGS. 1 and 2, during the manufacture of semiconductor devices. The ellipsometric measurements made in the instrument error correction configuration of the ellipsometer are preferably performed immediately prior to or after the ellipsometric measurements made of the sample in the sample measurement configuration to minimize any changes in the error caused by the ellipsometer as a function of time, e.g. with temperature changes, for example. The results of measurements using the ellipsometer 20 are depicted in FIG. 6 of the drawing wherein measurements are shown before and after correction for non-sample optical system ellipsometric effects. The sample optical system in this case is an 80 angstrom layer of silicon dioxide on a silicon substrate. The measured parameter is the thickness of silicon dioxide. In this experiment the focusing optic, 5 in FIGS. 1–4, was subjected to mechanical stress which is known to induce non-sample optical system ellipsometric errors into the ellipsometer. The induced stress is shown increasing across the horizontal axis from left to right. The vertical axis shows the deviation from the expected result before and after correction of the measurement using the error correction mode. In this experiment the residual error of the corrected measurements is in part a result of making measurements before the induced mechanical stresses are fully redistributed in the focusing optic, 5.

The ellipsometer 20, according to the invention, can also be provided with a dispersing element, not shown, as discussed with reference to FIG. 5 in U.S. Pat. No. 5,166,752 to enable the simultaneous detection of the beam as a function of angle of incidence and wavelength without scanning either. In the ellipsometer 20 depicted in the drawing as well as this variation thereof, the ellipsometry method and ellipsometer of the invention provide a method and means for separation of instrument error from the measured properties while at the same time allowing for simultaneous measurement of multiple angles of incidence and/or of multiple wavelengths of light. The movement of the convex spherical mirror 6 into the optical path in front of the focusing optic 5 switches the ellipsometer to an error correction mode for the instrument error measurement. Rapid, successive measurements can be made with and without this element in the optical path under the control of microprocessor 21 to allow for the determination and cancellation of all non-sample ellipsometric effects in the manner described. All rays on both spherical mirrors 6 and 8 are at normal incidence.

The stage 16 at which the sample 7 is positioned is preferably adjustable in the x, y and z directions as shown schematically in FIGS. 1 and 4 as mentioned above. Fine adjusters can also be provided on the optical components of the ellipsometer, including the focusing optic 5 for ensuring spot coincidence of the focused beam initially reflected from the surface of the sample 7 and that re-reflected by the concave mirror 8. As a result of these and other features of the invention, separation of instrument error from the measured properties can be accomplished to provide more accurate measurements and more measurement capability in a relatively simple manner as compared with conventional ellipsometers and ellipsometric methods.

Figure 7:
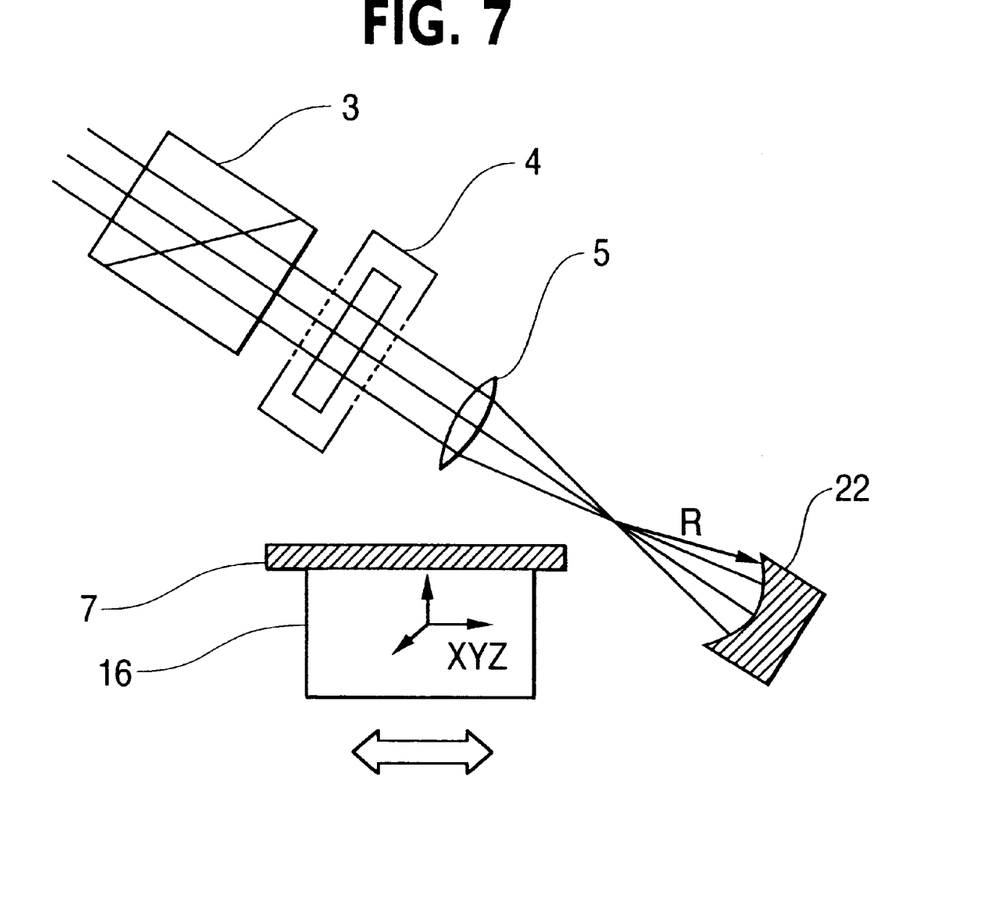
FIG. 7 is a schematic illustration of an ellipsometer like that in FIG. 1, but with the convex mirror thereof being replaced by a concave mirror.
Figure 8:
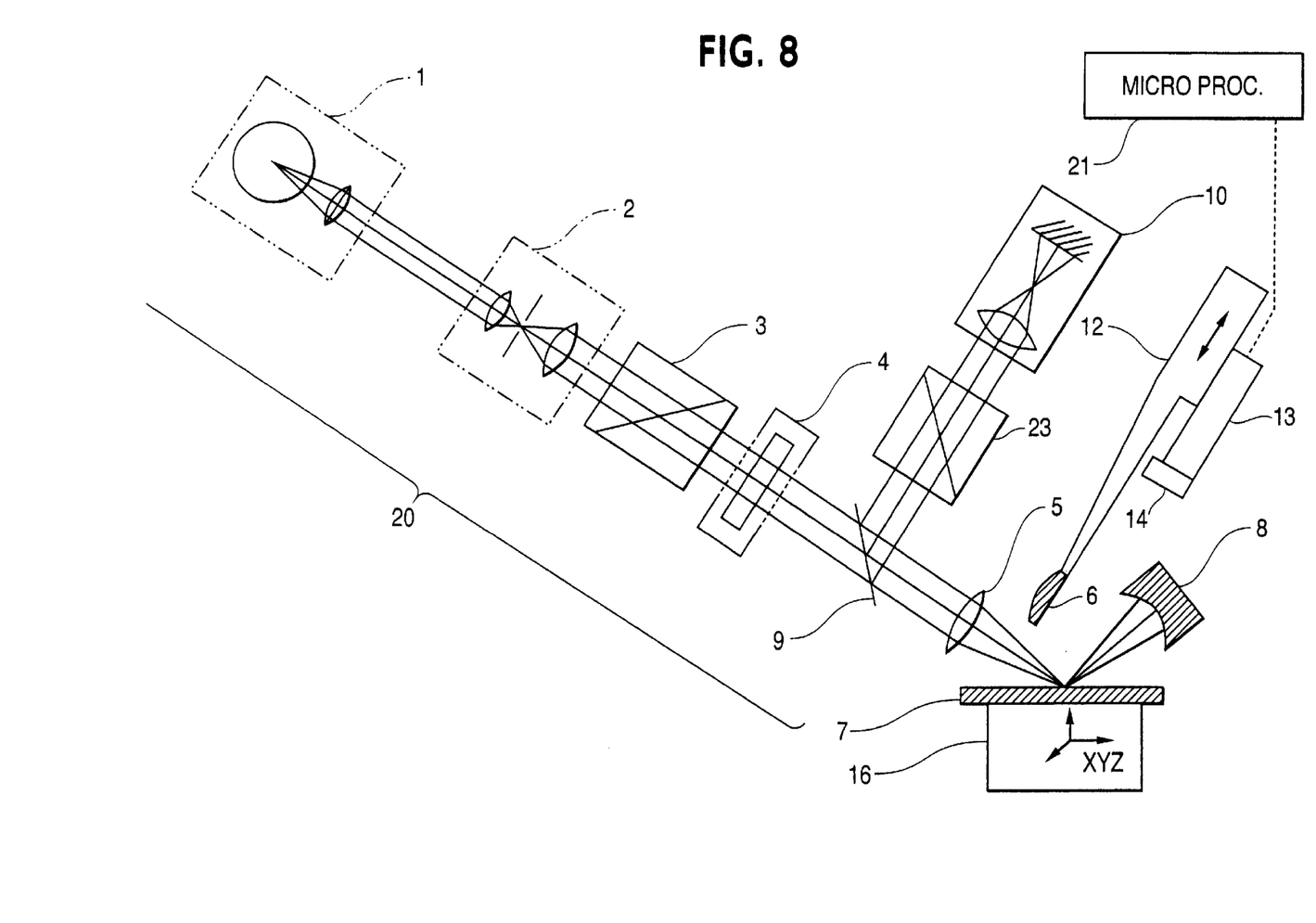
FIG. 8 is a schematic illustration of a further variation of the ellipsometer of FIG. 1, wherein the array detector and an analyzer are located between the sample and the polarization modulation section rather than further outward along the optical path from the light source as in the ellipsometer of FIG. 1.

While I have shown and described only certain embodiments in accordance with the present invention, it is understood that the same is not limited thereto, but is susceptible to numerous changes and modifications as known to those skilled in the art. One possible variation is to replace the convex mirror 6 with a concave mirror, 22 in FIG. 7, having a center of curvature coincident with a focal point of focusing optic 5 of the ellipsometer focusing the single beam of light at a single point on the sample optical system with constituent light rays forming the plurality of angles of incidence with the sample optical system. In such case, the concave mirror 22 would be fixed such that when the sample optical system 7 is removed from the optical path by stage 16 as shown in FIG. 7, the rays after striking the concave mirror 22 retrace their path through the focusing optic 5.

As noted above, the ellipsometer and ellipsometry method of the invention are also not limited to multi-angle ellipsometry, but have applicability to return path ellipsometry and ellipsometers including hybrid systems that can operate in a return path mode and another mode such as a single-pass ellipsometer, for example. The error introduced by a vacuum window(s) in a vacuum compatible ellipsometer according to the invention can be corrected with the method and ellipsometer of the invention. See vacuum window/chamber 24 shown schematically in FIG. 2.

Therefore, I do not wish to be limited to the details shown and described herein, but intend to cover all such changes and modifications as are encompassed by the scope of the appended claims.

I claim:

1. An ellipsometry method comprising operating an ellipsometer to direct polarized light so that the light interacts with a sample optical system under study more than once by reflection of the polarized light from a surface of the sample optical system and re-reflection of the reflected light from said surface of the sample optical system so as to retrace its path in said ellipsometer, and measuring a change in polarization state of the light interacted with the sample optical system, wherein said polarized light includes a single beam of light which is simultaneously directed to interact with the sample optical system at different angles of incidence and wherein a change in polarization state is measured for at least one of a plurality of said angles of incidence of the multiple interactions of the light with the sample optical system, and wherein said ellipsometer is a return-path ellipsometer with a polarizer arm and an analyzer arm superimposed on said polarizer arm and wherein said step of directing said polarizer light to interact with the optical system at different angles of incidence includes reflecting said light from a surface of the sample optical system and re-reflecting said reflected light from said surface of said sample optical system so that said re-reflected light retraces its path in said arm of said ellipsometer and is then separated from the originating beam to be measured. and wherein said ellipsometer is a return-path ellipsometer with a polarizer arm and an analyzer arm superimposed on said polarizer arm and wherein said step of directing said polarized light to interact with the optical system at different angles of incidence includes reflecting said light from a surface of the sample optical system and re-reflecting said reflected light from said surface of said sample optical system so that said re-reflected light retraces its path in said arm of said ellipsometer and is then separated from the originating beam to be measured.

2. The ellipsometry method according to claim 1, wherein a nominal angle of said single beam of light with respect to said sample optical system is oblique.

3. The ellipsometry method according to claim 1, wherein a nominal angle of said single beam of light with respect to said sample optical system is normal.

4. The ellipsometry method according to claim 1, wherein the polarized light is monochomatic.

5. The ellipsometry method according to claim 1, wherein the polarized light polarized is polychromatic.

6. The ellipsometry method according to claim 1, wherein said reflected polarized light is re-reflected from a surface of said sample optical system using a concave reflector.

7. The ellipsometry method according to claim 1, further comprising measuring non-sample optical system ellipsometric effects of said ellipsometer and correcting said measured change in polarization state of the light interacted with the sample optical system to eliminate error introduced therein by said non-sample optical system ellipsometric effects.

8. The ellipsometry method according to claim 1, wherein said polarized light-is reflected and re-reflected from the same spot on the surface of said sample optical system under study.

9. An ellipsometry method comprising operating a return path ellipsometer to direct polarized light so that polarized light in a single beam simultaneously interacts with a sample optical system under study at a plurality of different angles of incidence and subsequently said light is reflected back to and again interacts with said sample optical system, and measuring a change in polarization state of the light interacted with the sample optical system, said said method further including reflecting polarized light from said ellipsometer which has not interacted with said sample optical system back through a polarizing arm of the ellipsometer and measuring non-sample optical ellipsometric effects of said ellipsometer, and correcting said measured change in polarization state of the light interacted with the sample using said measured non-sample optical ellipsometric effects to eliminate error introduced in said measured change in polarization state by said non-sample optical system ellipsometric effects.

10. The ellipsometry method according to claim 9, wherein said sample optical system is in a vacuum, said ellipsometer being vacuum compatible and said step of correcting including removing the error induced by the vacuum compatible ellipsometer.

11. A return path ellipsometer comprising means for directing polarized light so that the light travels along a path and simultaneously interacts with a sample optical system under study at a plurality of angles of incidence and after said interacting said light is reflected back along said path and further interacts with said sample optical system, means for measuring a change in polarization state of said light interacted with the sample optical system and means for measuring non-sample optical system ellipsometric effects of said ellipsometer using polarized light which travels along said path but does not interact with said sample optical system to allow correction of said measured change in polarization state of the light interacted with the sample optical system to eliminate error introduced therein by said non-sample optical system ellipsometric effects.

12. The ellipsometer according to claim 11, wherein said ellipsometer can operate both in a return path mode and as a single pass ellipsometer.

13. The ellipsometer according to claim 11, wherein said ellipsometer is a vacuum compatible ellipsometer and said means for measuring non-sample optical system ellipsometric effects allows removing the error induced as a result of said vacuum compatibility.

14. An ellipsometry method comprising operating a simultaneous multiple angle of incidence ellipsometer to direct polarized light so that the light interacts with a sample optical system under study and measuring a change in polarization state of the light interacted with the sample optical system, wherein polarized light from a single beam of light is simultaneously directed to interact with the sample optical system at different angles of incidence and wherein a change in polarization state is measured for at least one of a plurality of said angles of incidence, said method including measuring non-sample optical system ellipsometric effects of said ellipsometer by reflecting polarized light from said ellipsometer which has not interacted with said sample optical system so that said reflected light retraces its path in said ellipsometer, and correcting said measured change in polarization state of the light interacted with the sample optical system to eliminate error introduced therein by said non-sample optical system ellipsometric effects.

15. The ellipsometry method according to claim 14, wherein said step of measuring non-sample optical system ellipsometric effects of said ellipsometer includes operating said ellipsometer in an error correction mode.

16. The ellipsometry method according to claim 14, wherein said ellipsometer is a return-path ellipsometer with a polarizer arm and an analyzer arm superimposed on or sharing some components with said polarizer arm and wherein said step of directing said polarized light to interact with the optical system at different angles of incidence includes reflecting said light from a surface of the sample optical system and re-reflecting said reflected light from said surface of said sample optical system so that it retraces its path in said arm of said ellipsometer.

17. The ellipsometry method according to claim 16, wherein said step of measuring non-sample optical system ellipsometric effects of said ellipsometer includes reflecting said beam of polarized light to cause the light rays at each of said plurality of angles of incidence in said beam to retrace the path of the light rays in said arm of the ellipsometer without undergoing said reflection and re-reflection from said surface of said sample optical system.

18. The ellipsometry method according to claim 17, including inserting and removing a reflector from said optical path of said beam of polarized light directed toward said sample optical system to permit said measuring of said non-sample optical system ellipsometric effects.

19. The ellipsometry method according to claim 17, including removing said optical system under study from said optical path to perform said step of measuring non-sample optical system ellipsometric effects to allow said beam to be reflected by a reflector to retrace its path in said arm of the ellipsometer without undergoing reflection and re-reflection from said surface of said sample optical system.

20. The ellipsometry method according to claim 14, including modulating the polarization state of said light beam during said measuring steps.

21. The ellipsometry method according to claim 14, wherein said measuring non-sample optical system ellipsometric effects of said ellipsometer is performed in relatively close time sequence with said measuring a change in polarization state of the light interacted with the sample optical system at said at least one angle of incidence.

22. The ellipsometry method according to claim 14, wherein each of said measuring steps includes detecting the intensity of reflected polarized light at each of a plurality of said angles of incidence.

23. The ellipsometry method according to claim 14, wherein said beam of polarized light directed to interact with the optical system at said different angles of incidence is entirely oblique with respect to the surface of said optical system with which said light interacts.

24. The ellipsometry method according to claim 14, wherein the light is directed onto a surface of the optical system under study at a single spot with a cone of polarized light derived from a single beam.

25. An ellipsometer comprising means for directing polarized light so that the light interacts with a sample optical system under study in a vacuum chamber through a vacuum window of said vacuum chamber, and means for measuring a change in polarization state of said light interacted with the sample optical system under study, wherein said means for directing polarized light includes means for simultaneously directing polarized light from a single beam of light onto the optical system under study at different angles of incidence, and wherein said means for measuring measures a change in polarization state of light interacted with the sample optical system under study for at least one of a plurality of said different angles of incidence, and said ellipsometer further including means for measuring non-sample optical system ellipsometric effects of said ellipsometer including the error introduced by said vacuum window to allow correction of said measured change in polarization state of the light interacted with the sample optical system to eliminate error introduced therein by said non-sample optical system ellipsometric effects.

26. An ellipsometer according to claim 25, wherein said means for measuring non-sample optical system ellipsometric effects includes means for operating said ellipsometer in an error correction mode.

27. An ellipsometer according to claim 25, wherein said ellipsometer is a return-path ellipsometer having a polarizer arm and an analyzer arm superimposed on said polarizer arm and wherein said means for measuring a change in polarization state of light interacted with the sample optical system under study for at least one of said plurality of angles of incidence reflects said light from a surface of the sample optical system and re-reflects said reflected light from said surface of said sample optical system so that it retraces it path in said arm of said ellipsometer.

28. An ellipsometer according to claim 27, wherein said means for measuring non-sample optical system ellipsometric effects includes a reflector which can be inserted in a position in the optical path of said beam of polarized light directed toward said sample optical system at different angles of incidence to cause the light rays at each of said plurality of angles of incidence in said beam to retrace its path in said arm of the ellipsometer without undergoing said reflection and re-reflection from said surface of said sample optical system.

29. An ellipsometer according to claim 28, wherein said reflector is a convex mirror having a center of negative curvature thereof coincident with a focal point of a focusing optic of said ellipsometer focusing said single beam of light at a single point on the sample optical system with constituent light rays forming said plurality of angles of incidence with said sample optical system.

30. An ellipsometer according to claim 28, further comprising means for moving said reflector into and out of said position in said optical path.

31. An ellipsometer according to claim 28 wherein said reflector is a concave mirror having a center of curvature thereof coincident with a focal point of a focusing optic of said ellipsometer focusing said single beam of light at a single point on the sample optical system with constituent light rays forming said plurality of angles of incidence with said sample optical system, said concave mirror being fixed such that when the sample optical system is removed from the optical path the rays after striking said concave mirror retrace the incidence path of said light rays through the focusing optic.

32. An ellipsometer according to claim 28, including means for modulating the polarization of said polarized light.

33. A return path ellipsometer comprising a source of a beam of polarized light which can be directed along an optical path in said ellipsometer, a focusing optic for focusing said beam of polarized light so that the beam is simultaneously incident on a sample optical system under study at different angles of incidence for reflection therefrom, a concave reflector located in an optical path of the beam of light reflected from said sample optical system under study for re-reflecting said reflected light from said sample optical system so that said re-reflected light retraces its path through said focusing optic, a detector array for detecting the intensity of said light re-reflected through said focusing optic for each of a plurality of said different angles of incidence, and a convex reflector which can be inserted into and removed from the optical path of said beam of polarized light between said focusing optic and said sample optical system under study, said convex reflector being configured so that when inserted into said optical path it causes the light rays of said beam of polarized light at each of said plurality of angles of incidence to retrace its path through said focusing optic without undergoing reflection and re-reflection from said sample optical system for detection by said detector array.

34. A return path ellipsometer according to claim 33, further comprising a beam splitter for directing a portion of said light which has retraced its path through said focusing optic to said detector array.

35. A return path ellipsometer according to claim 33, wherein said source of a beam of polarized light includes a light source, beam shaping optics including a spatial filtering beam expander, and a fixed polarizer arranged on an optical path of said light in said ellipsometer.

36. A return path ellipsometer according to claim 35, further comprising a beam splitter located between said source of a beam of polarized light and said focusing optic for directing a portion of said light which has retraced its path through said focusing optic to an analyzer arm consisting of a second fixed polarizer and said detector array.

37. A return path ellipsometer according to claim 33, wherein a center of curvature of said concave reflector is coincident with a point on said sample optical system illuminated by said focused beam while said convex reflector is removed from said optical path.

38. A return path ellipsometer according to claim 33, wherein a center of negative curvature of said convex reflector is coincident with a focal point of said focusing optic when said convex reflector is inserted into said optical path.

39. A return path ellipsometer according to claim 33, further comprising a modulator for modulating the polarization state of said polarized light from said light source before focusing said beam with said focusing optic.

40. A return path ellipsometer according to claim 33, further comprising a mechanism for moving said convex reflector into and removing it from said optical path.

41. An ellipsometry method comprising:

directing a beam of polarized light along an optical path;

focusing said beam of polarized light onto a sample optical system under study so that the beam is simultaneously incident on the sample optical system at different angles of incidence for reflection therefrom;

re-reflecting said reflected light from said sample optical system so that said re-reflected light retraces said optical path;

detecting the intensity of said re-reflected light for each of a plurality of said different angles of incidence using a detector array; and wherein said method further includes inserting a reflector into said optical path to cause the light rays of said beam of polarized light at each of said plurality of angles of incidence to retrace its path along said optical path without undergoing reflection and re-reflection from said sample optical system for detection by said detector array.

* * * * *

UNITED STATES PATENT AND TRADEMARK OFFICE
CERTIFICATE OF CORRECTION

PATENT NO. : 6,256,097 B1 Page 1 of 1
APPLICATION NO. : 09/478795
DATED : July 3, 2001
INVENTOR(S) : Wagner

It is certified that error appears in the above-identified patent and that said Letters Patent is hereby corrected as shown below:

Col. 8 Line 44-54 should read,

1. An ellipsometry method comprising operating an ellipsometer to direct polarized light so that the light interacts with a sample optical system under study more than once by reflection of the polarized light from a surface of the sample optical system and re-reflection of the reflected light from said surface of the sample optical system so as to retrace its path in said ellipsometer, and measuring a change in polarization state of the light interacted with the sample optical system, wherein said polarized light includes a single beam of light which is simultaneously directed to interact with the sample optical system at different angles of incidence and wherein a change in polarization state is measured for at least one of a plurality of said angles of incidence of the multiple interactions of the light with the sample optical system, and wherein said ellipsometer is a return-path ellipsometer with a polarizer arm and an analyzer arm superimposed on said polarizer arm and wherein said step of directing said polarizer light to interact with the optical system at different angles of incidence includes reflecting said light from a surface of the sample optical system and re-reflecting said reflected light from said surface of said sample optical system so that said re-reflected light retraces its path in said arm of said ellipsometer and is then separated from the originating beam to be measured. ~~and wherein said ellipsometer is a return-path ellipsometer with a polarizer arm and an analyzer arm superimposed on said polarizer arm and wherein said step of directing said polarized light to interact with the optical system at different angles of incidence includes reflecting said light from a surface of the sample optical system and re-reflecting said reflected light from said surface of said sample optical system so that said re-reflected light retraces its path in said arm of said ellipsometer and is then separated from the originating beam to be measured.~~

Signed and Sealed this

Fourteenth Day of July, 2009

JOHN DOLL
*Acting Director of the United States Patent and Trademark Office*